(12) United States Patent
Ceccarelli et al.

(10) Patent No.: US 8,785,663 B2
(45) Date of Patent: Jul. 22, 2014

(54) POLYMORPHIC FORMS OF LUBIPROSTONE

(76) Inventors: Alfredo Paul Ceccarelli, Brantford (CA); Kiran Kumar Kothakonda, Brantford (CA)

( * ) Notice: Subject to any disclaimer, the term of this patent is extended or adjusted under 35 U.S.C. 154(b) by 0 days.

(21) Appl. No.: 13/575,680

(22) PCT Filed: Jan. 28, 2011

(86) PCT No.: PCT/CA2011/000088
§ 371 (c)(1),
(2), (4) Date: Nov. 20, 2012

(87) PCT Pub. No.: WO2011/091513
PCT Pub. Date: Aug. 4, 2011

(65) Prior Publication Data
US 2013/0096325 A1    Apr. 18, 2013

Related U.S. Application Data

(60) Provisional application No. 61/299,176, filed on Jan. 28, 2010.

(51) Int. Cl.
*C07D 311/94*    (2006.01)

(52) U.S. Cl.
USPC .......................................... 549/396

(58) Field of Classification Search
CPC ............ A61K 31/558; C07B 2200/13; C07B 405/00; C07D 311/94
USPC ........................................... 549/396
See application file for complete search history.

(56)    References Cited

U.S. PATENT DOCUMENTS

2011/0028541 A1*    2/2011    Tang et al. ................... 514/456
2011/0112312 A1*    5/2011    Alberico et al. .............. 549/299

FOREIGN PATENT DOCUMENTS

WO    WO 2009/121228 A2 *    10/2009
WO    WO 2010083597             7/2010

OTHER PUBLICATIONS

Viscomi, G.C., Crystal forms of rifaximin and their effect on pharmaceutical properties (2008) Cryst. Eng. Commun. 10: 1074-1081.*

* cited by examiner

*Primary Examiner* — Kortney L Klinkel
*Assistant Examiner* — John Mauro

(57)    ABSTRACT

There is provided a crystalline form of Lubiprostone, termed APO-II and methods for making APO-II. APO-II is a polymorphic form of Lubiprostone.

20 Claims, 3 Drawing Sheets

POLYMORPHIC FORMS OF LUBIPROSTONE

TECHNICAL FIELD

The present invention relates to polymorphic forms of Lubiprostone.

BACKGROUND

Lubiprostone (1) is an E1 type prostaglandin derivative. It is marketed in USA as Amitiza® and is used for the treatment of idiopathic chronic constipation, irritable bowel syndrome and post operative ilues. The use of Lubiprostone softens the stool, increases motility, and promotes spontaneous bowel movements (SBM). Chemically, Lubiprostone is 7-[(2R,4aR, 5R,7aR)-2-(1,1-difluoropentyl)-2-hydroxy-6-oxooctahydrocyclopenta[b]pyran-5-yl]heptanoic acid (*Drugs of the Future*, 2004, 29(4); 336-341):

LUBIPROSTONE (1)

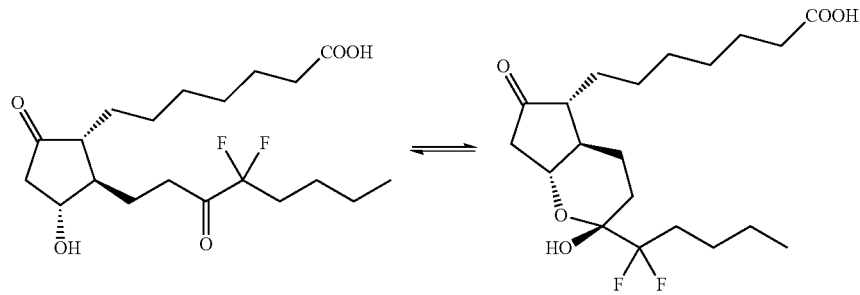

U.S. Pat. No. 5,117,042 discloses a method of treatment for improving encephalic function which comprises administering to a subject in need of such treatment a 15-keto-prostaglandin compound in an amount effective for improvement of encephalic function.

U.S. Pat. No. 5,284,858 discloses 13,14-dihydro-15-keto prostaglandins E having remarkable preventive effects against ulcers. Further, according to U.S. Pat. No. 5,284,858, 13,14-dihydro-15-ketoprostaglandins E have an advantage that they have none of the side effects which prostaglandin E intrinsically has, or can remarkably reduce such effects of the prostaglandin E. According to U.S. Pat. No. 5,284,858, 13,14-dihydro-15-keto prostaglandins E are effective for animal and human use for treatment and prevention of ulcers, such as duodenal ulcer and gastric ulcer.

U.S. Pat. No. 6,414,016 provides an anti-constipation composition containing a halogenated-bi-cyclic compound as an active ingredient in a ratio of bi-cyclic/mono-cyclic structure of at least 1:1. The halogenated-bi-cyclic compound in U.S. Pat. No. 6,414,016 is represented by Formula (I):

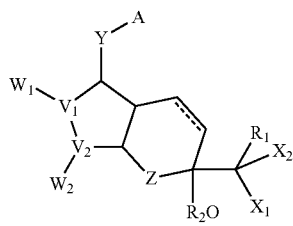

where X1 and X2 are preferably both fluorine atoms. According to U.S. Pat. No. 6,414,016, the composition can be used to treat constipation without substantive side-effects, such as stomachache.

WO2009/121228 discloses a Lubiprostone crystal, its preparation process, its pharmaceutical composition or kit, and its use for the preparation of a pharmaceutical composition for treating gastroenteropathy, especially constipation. According to WO2009/121228, the characteristic peaks of 2θ reflection angle in X-ray powder diffraction spectra of the crystal include 14.6±0.2°, 17.0±0.2° and 19.6±0.2°. According to WO2009/121228, the crystal has the advantages of high purity, stable property, and convenient storage and usage compared with amorphous Lubiprostone.

SUMMARY

The present invention relates, at least in part, to a crystalline form of Lubiprostone, namely a polymorphic form of Lubiprostone termed herein as APO-II and to processes for preparing APO-II.

Illustrative embodiments of the present invention provide a crystalline form of Lubiprostone having an X-ray powder diffraction pattern comprising a peak, in terms of 2-theta, at approximately 8.98.

Illustrative embodiments of the present invention provide a crystalline form of Lubiprostone having an X-ray powder diffraction pattern comprising a peak, in terms of 2-theta, at approximately 13.53.

Illustrative embodiments of the present invention provide a crystalline form of Lubiprostone having an X-ray powder diffraction pattern comprising a peak, in terms of 2-theta, at approximately 18.06.

Illustrative embodiments of the present invention provide a crystalline form of Lubiprostone having an X-ray powder diffraction pattern comprising a peak, in terms of 2-theta, at approximately 20.57.

Illustrative embodiments of the present invention provide a crystalline form of Lubiprostone having an X-ray powder diffraction pattern comprising a peak, in terms of 2-theta, at approximately 20.80.

Illustrative embodiments of the present invention provide a crystalline form of Lubiprostone having an X-ray powder diffraction pattern comprising a peak, in terms of 2-theta, at approximately 22.74.

Illustrative embodiments of the present invention provide a crystalline form of Lubiprostone having an X-ray powder diffraction pattern comprising a peak, in terms of 2-theta, at approximately 13.53 together with any one or more peaks described herein.

Illustrative embodiments of the present invention provide a crystalline form of Lubiprostone having an X-ray powder diffraction pattern comprising a peak, in terms of 2-theta, at approximately 18.06 together with any one or more peaks described herein Illustrative embodiments of the present invention provide a crystalline form of Lubiprostone having an X-ray powder diffraction pattern comprising a peak, in terms of 2-theta, at approximately 20.57 together with any one or more peaks described herein Illustrative embodiments of the present invention provide a crystalline form of Lubiprostone having an X-ray powder diffraction pattern comprising a peak, in terms of 2-theta, at approximately 20.80 together with any one or more peaks described herein Illustrative embodiments of the present invention provide a crystalline form of Lubiprostone having an X-ray powder diffraction pattern comprising a peak, in terms of 2-theta, at approximately 22.74 together with any one or more peaks described herein Illustrative embodiments of the present invention provide a crystalline form of Lubiprostone having an X-ray powder diffraction pattern substantially as shown in FIG. 1.

Illustrative embodiments of the present invention provide a crystalline form of Lubiprostone having a 1% KBr FTIR spectrum comprising peaks, in terms of $cm^{-1}$, at approximately 3470, 2938, 1738, 1710, 1473, 1383, 1313, 1210, 1159, 979, 891, 793, 726 and 580.

Illustrative embodiments of the present invention provide a crystalline form of Lubiprostone having a FTIR spectrum substantially as shown in FIG. 2.

Illustrative embodiments of the present invention provide a crystalline form of Lubiprostone having a DSC thermogram comprising an endothermic peak with a peak onset temperature of approximately 76° C. and a peak maximum of approximately 77° C.

Illustrative embodiments of the present invention provide a crystalline form of Lubiprostone having a DSC thermogram substantially as shown in FIG. 3.

Illustrative embodiments of the present invention provide a process to prepare APO-II comprising: distilling a Lubiprostone filtrate to near dryness thereby forming a residue; dissolving the residue in a first organic solvent thereby forming a residue solution; adding a second organic solvent to the residue solution thereby forming a mixture; stirring the mixture until precipitation occurs thereby forming a precipitate; filtering the precipitate thereby isolating APO-II.

Illustrative embodiments of the present invention provide a process to prepare APO-II comprising: dissolving Lubiprostone in a third organic solvent thereby forming a Lubiprostone solution; adding a fourth organic solvent to the Lubiprostone solution thereby forming a mixture; stirring the mixture until precipitation occurs thereby forming a precipitate; filtering the precipitate thereby isolating APO-II.

Illustrative embodiments of the present invention provide a process to prepare APO-II comprising: dissolving Lubiprostone in a third organic solvent thereby forming a Lubiprostone solution; adding the Lubiprostone solution to a fourth organic solvent thereby forming a mixture; stirring the mixture until precipitation occurs thereby forming a precipitate; filtering the precipitate thereby isolating APO-II.

Illustrative embodiments of the present invention provide a pharmaceutical formulation comprising APO-II.

Other aspects and features of the present invention will become apparent to those ordinarily skilled in the art upon review of the following description of specific embodiments of the invention with the accompanying figures.

BRIEF DESCRIPTION OF THE DRAWINGS

Drawings which illustrate embodiments of the invention are.

DETAILED DESCRIPTION

Figure 1:
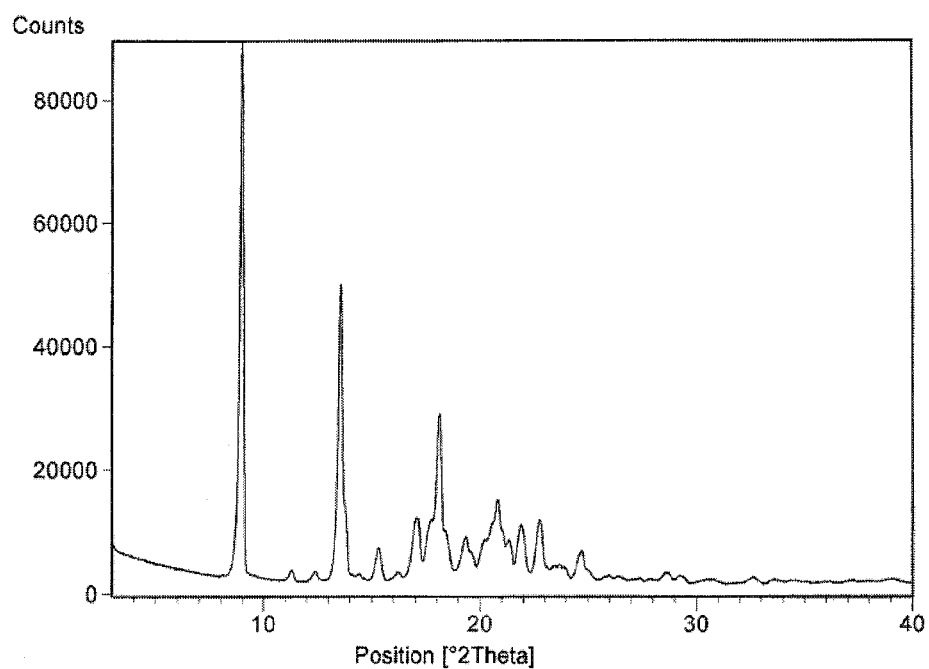
FIG. 1: is a powder X-ray diffraction (PXRD) diffractogram of APO-II.

When used in reference to a diffractogram, a spectrum and/or data presented in a graph, the term "substantially similar" means that the subject diffractogram, spectrum and/or data presented in a graph encompasses all diffractograms, spectra and/or data presented in graphs that vary within acceptable boundaries of experimentation that are known to a person of skill in the art. Such boundaries of experimentation will vary depending on the type of the subject diffractogram, spectrum and/or data presented in a graph, but will nevertheless be known to a person of skill in the art.

When used in reference to a peak in a powder X-ray diffraction (PXRD) diffractogram, the term "approximately" means that the peak may vary by ±0.2 degrees 2θ of the subject value.

When used in reference to a peak in a Fourier transform infrared (FTIR) spectrum, the term "approximately" means that the peak may vary by ±5 $cm^{-1}$ of the subject value.

When used in reference to a peak in a differential scanning calorimetry (DSC) thermogram, the term "approximately" means that the peak may vary by ±1 degree of the subject value.

As used herein when referring to a diffractogram, spectrum and/or to data presented in a graph, the term "peak" refers to a feature that one skilled in the art would recognize as not attributing to background noise.

Depending on the nature of the methodology applied and the scale selected to display results obtained from an X-ray diffraction analysis, an intensity of a peak obtained may vary quite dramatically. For example, it is possible to obtain a relative peak intensity of 0.01% when analyzing one sample of a substance, but another sample of the same substance may show a much different relative intensity for a peak at the same position. This may be due, in part, to the preferred orientation of the sample and its deviation from the ideal random sample orientation, sample preparation and the methodology applied. Such variations are known and understood by a person of skill in the art.

In an illustrative embodiment, the present invention comprises a crystalline form of Lubiprostone which is a polymorphic form referred to herein as APO-II. An illustrative PXRD diffractogram of APO-II is given in FIG. 1. An illustrative FTIR spectrum of APO-II is given in FIG. 2. An illustrative DSC thermogram of APO-II is given in FIG. 3. Illustrative relative peak intensities of APO-II are illustrated below in Table 1.

TABLE 1

Relative Peak Intensities for APO-II

| 2θ | Relative Peak Intensity (±10%) |
|---|---|
| 8.98 | 100 |
| 13.53 | 53 |

TABLE 1-continued

Relative Peak Intensities for APO-II

| 2θ | Relative Peak Intensity (±10%) |
| --- | --- |
| 17.10 | 12 |
| 17.63 | 11 |
| 18.06 | 27 |
| 18.13 | 32 |
| 20.57 | 11 |
| 20.80 | 14 |
| 20.83 | 14 |
| 21.88 | 11 |
| 22.74 | 11 |

According to illustrative embodiments of the present invention, APO-II may be prepared according to Scheme 1.

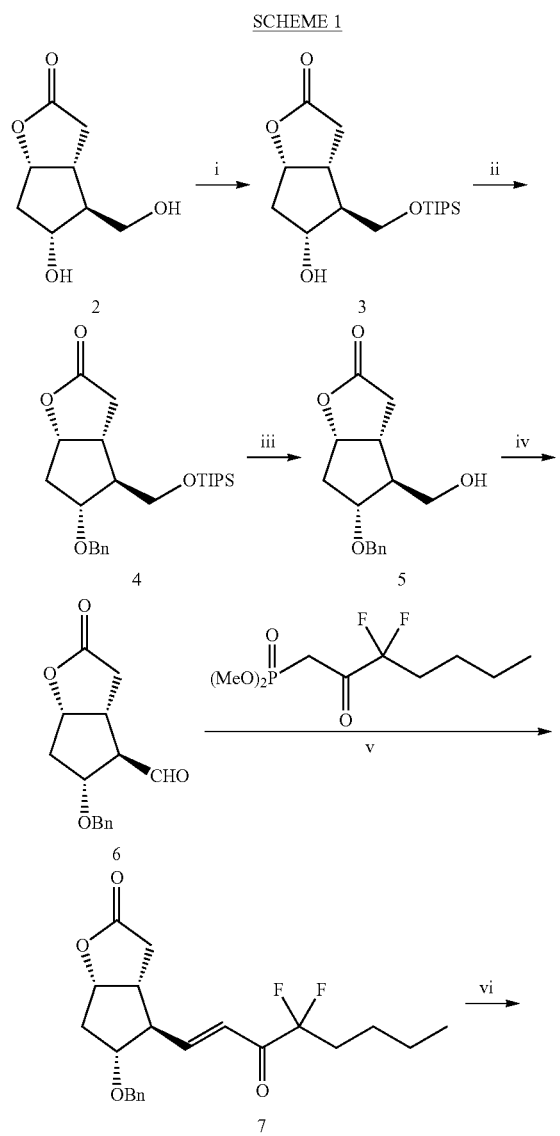

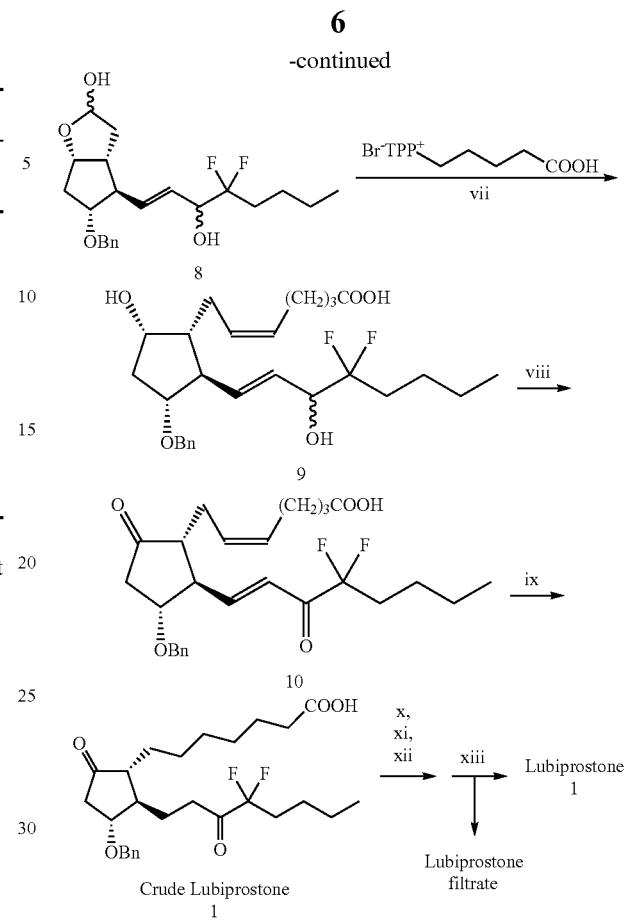

i) TIPS-Cl, imidazole, $CH_2Cl_2$; ii) BnBr, NaH, THF; (iii) TBAF, THF; iv) oxalyl chloride, DMSO, $CH_2Cl_2$ v) aq. $Zn(OH)_2$, MTBE, $CH_2Cl_2$; vi) DIBAL-H, $CH_2Cl_2$; vii) $K^tOBu$, THF; viii) Dess-Martin periodinane, $CH_2Cl_2$; ix) 10% Pd—C, $H_2$, $CH_2Cl_2$; x) purification by column chromatography (EtOAc/Hexanes): xi) t-butylamine, EtOAc, pet ether; xii) HCOOH, water, EtOAc; xiii) EtOAc, pet. ether.

Starting from commercially available lactone 2, Lubiprostone may be prepared, for instance, as illustrated in Scheme 1. The Lubiprostone filtrate referred to in Scheme 1 may be a starting material for use in making APO-II. The present invention provides a process of preparing APO-II comprising:

a. distilling the Lubiprostone filtrate to near dryness thereby forming a residue;
b. dissolving the residue in a first organic solvent thereby forming a residue solution;
c. optionally filtering the residue solution thereby forming a filtered residue solution;
d. adding a second organic solvent to the residue solution and/or the filtered residue solution thereby forming a residue mixture;
e. maintaining the residue mixture until precipitation occurs thereby forming a precipitate;
f. filtering the precipitate thereby isolating APO-II; and
g. optionally drying APO-II.

The first organic solvent used to dissolve the residue may be any organic solvent. Often the first organic solvent may be ethyl acetate, methyl tert-butyl ether (MTBE) and mixtures thereof. The volume of the first organic solvent may be about 0.5 volumes to about 5 volumes. The volume of the first organic solvent may be about 0.5 volumes to about 1.5 volumes.

The second organic solvent used may be any organic solvent which exhibits anti-solvent properties with Lubiprostone. Often the second organic solvent is petroleum ether, hexanes, heptanes or mixtures thereof. The volume of the second organic solvent may be about 1 volumes to about 15 volumes. The volume of the second organic solvent may be about 3 volumes to about 10 volumes.

The precipitation of APO-II may be performed at a temperature of about 5° C. to about 40° C. The temperature for precipitation may be about 15° C. to about 30° C. Often the temperature for precipitation is about 20° C. to about 25° C.

In another illustrative embodiment, the present invention provides a process of preparing APO-II comprising:
  h. dissolving Lubiprostone in a third organic solvent to form a Lubiprostone solution;
  i. optionally filtering the Lubiprostone solution thereby forming a filtered Lubiprostone solution;
  j. adding a fourth organic solvent to the Lubiprostone solution and/or to the filtered Lubiprostone solution thereby forming a Lubiprostone mixture; or alternatively adding the Lubiprostone solution and/or the filtered Lubiprostone solution to the fourth organic solvent thereby forming the Lubiprostone mixture;
  k. optionally adding APO-II to the Lubiprostone mixture;
  l. stirring the Lubiprostone mixture until precipitation occurs thereby forming a precipitate;
  m. filtering the precipitate thereby isolating APO-II; and
  n. optionally drying APO-II.

The Lubiprostone dissolved in step h may be any Lubiprostone (e.g. any polymorphic form and/or mixtures thereof).

The third organic solvent used to dissolve the Lubiprostone may be any organic solvent. Often the third organic solvent may be ethyl acetate, MTBE and mixtures thereof. The volume of the third organic solvent may be about 0.5 volumes to about 5 volumes. The volume of the third organic solvent may be about 0.5 volumes to about 1.5 volumes.

The fourth organic solvent used may be any organic solvent which exhibits anti-solvent properties with Lubiprostone. Often the fourth organic solvent is petroleum ether, hexanes, heptanes or mixtures thereof. The volume of the fourth organic solvent may be about 1 volumes to about 15 volumes. The volume of the fourth organic solvent may be about 3 volumes to about 10 volumes.

The precipitation of APO-II may be performed at a temperature of about 5° C. to about 40° C. The temperature for precipitation may be about 15° C. to about 30° C. Often the reaction temperature may be about 20° C. to about 25° C.

The amount of APO-II used in step k may be about 0.01 to about 50 w/w percent relative to the amount of Lubiprostone added in step k.

Following the above steps a-g and/or h-n, polymorphic Form APO-II Lubiprostone may be produced.

The following examples are illustrative of some of the embodiments of the invention described herein. These examples do not limit the spirit or scope of the invention in anyway.

EXAMPLES

Powder X-Ray Diffraction Analysis (PXRD): The data were acquired on a PANanalytical X-Pert Pro MPD diffractometer with fixed divergence slits and an X-Celerator RTMS detector. The diffractometer was configured in Bragg-Brentano geometry; data was collected over a 2 theta range of 3 to 40 using CuKα radiation at a power of 40 mA and 45 kV. CuKβ radiation was removed using a divergent beam nickel filter. A step size of 0.017 degrees was used. A step time of 50 seconds was used. Samples were rotated at 1 Hz to reduce preferred orientation effects. The samples were prepared by the back-loading technique.

Fourier Transform Infrared (FTIR) Analysis: The FTIR spectrum was collected at 4 cm$^{-1}$ resolution using a Perkin Elmer Paragon 1100 single beam FTIR instrument. The samples were intimately mixed in an approximately 1:100 ratio (w/w) with potassium bromide (KBr) using an agate mortar and pestle to a fine consistency; the mixture was compressed in a pellet die at a pressure of 4 to 6 tonnes for a period of time between 2 and 5 minutes. The resulting disk was scanned 4 times versus a collected background. Data was baseline corrected and normalized.

Differential Scanning calorimetry (DSC) Analysis: The DSC thermograms were collected on a Mettler-Toledo 821e instrument. Samples (1 to 5 mg) were weighed into a 40 µL aluminum pan and were crimped closed with an aluminum lid. The samples were analyzed under a flow of nitrogen (ca. 55 mL/min) at a scan rate of 10° C./minute.

Example 1

Preparation of APO-II

To a suspension of compound 2 [(3aR,4S,5R,6aS)-hexahydro-5-hydroxy-4-(hydroxymethyl)-2H-cyclopenta[b]furan-2-one] (250 g, 1.45 mol) in dichloromethane (5 volumes) was added imidazole (118.6 g, 1.74 mol) followed by triisopropylsilyl chloride (TIPS-Cl) (308 mL, 1.60 mol). The suspension was stirred for about 15 hours. After the consumption of the starting material, the reaction mixture was cooled to 0° C., water (2 volumes) was added and the pH adjusted to 3-4 using 1N hydrochloric acid. The organic layer was separated, washed with water (to pH 5-6) and brine, dried over sodium sulfate and concentrated to dryness to yield compound 3 [(3aR,4S,5R,6aS)-hexahydro-5-hydroxy-4-(triisopropylsilyloxymethyl)-2H-cyclopenta[b]furan-2-one] as a clear oil in quantitative yield.

To a suspension of 60% NaH (70 g, 1.75 mol) in anhydrous tetrahydrofuran (750 mL) at 0° C. was slowly added a solution of compound 3 (429 g, 1.306 mol) in tetrahydrofuran (750 mL). The mixture was then stirred at 0° C. for 0.5 hour and then allowed to warm to room temperature for 1 hour. The mixture was again cooled to 0° C. and benzyl bromide (273 g, 1.60 mol) and Bu$_4$NI (107.3 g, 0.3 mol) were added sequentially. After stirring for 15 hours at room temperature, the mixture was then cooled to 0° C. before quenching with saturated ammonium chloride solution (2 volumes). The organic layer was separated, washed with brine, dried over sodium sulfate and then concentrated to dryness under vacuum to yield crude product, which was further purified by column chromatography (35% ethyl acetate in heptanes) to produce compound 4 [(3aR,4S,5R,6aS)-hexahydro-4-(triisopropylsilyloxymethyl)-5-(phenylmethoxy)-2H-cyclopenta[b]furan-2-one] in 80% yield.

To a solution of compound 4 (490 g, 1.17 mol) in tetrahydrofuran (3 volumes) at 0° C. was added tert-butylammonium fluoride (TBAF) (1 L, 1.0 mol) and the mixture was stirred for 2 hours. After completion of the reaction, the mixture was concentrated to dryness and purified by column chromatography (55% ethyl acetate in heptanes) to yield compound 5 [(3aR,4S,5R,6aS)-hexahydro-4-(hydroxymethyl)-5-(phenylmethoxy)-2H-cyclopenta[b]furan-2-one] in quantitative yield.

To a solution of oxalyl chloride (165 mL, 1.91 mol) in dichloromethane (1.750 L) at −78° C., was added dimethylsulfoxide (DMSO) (270 mL, 3.82 mol) and the mixture was stirred for 15 minutes. A solution of compound 5 (250 g, 0.95 mol) in dichloromethane (35 mL) was then slowly added at −78° C. and the reaction mixture stirred for 0.5 hour. Triethylamine (1.2 L, 8.5 mol) was added at −78° C. and the mixture stirred for 0.5 hour. After completion of the reaction, the reaction mixture was washed with water (1 L), and the organic layer was concentrated to dryness under vacuum to furnish compound 6 [(3aR,4R,5R,6aS)-hexahydro-2-oxo-5-(phenylmethoxy)-2H-cyclopenta[b]furan-4-carboxaldehyde] in 83% yield.

To a mixture of dimethyl(3,3-difluoro-2-oxoheptyl)phosphonate (210 g, 0.81 mol) in methyl t-butyl ether/water (300/10 mL) was added Zn(OH)$_2$ (100 g, 0.81 mol) and the mixture was stirred under nitrogen for 1 hour. A solution of compound 6 (200 g, 0.77 mol) in dichloromethane (300 mL) was added and the mixture was stirred for 24 hours. After completion of the reaction, the reaction was then quenched with cold 1N hydrochloric acid (120 mL). The organic layer was separated, washed with brine, dried over sodium sulfate and concentrated to dryness under vacuum. The crude material was further purified by column chromatography (25% ethyl acetate in heptanes) to yield compound 7 [(3aR,4R,5R,6aS)-4-((E)-4,4-difluoro-3-oxo-1-octenyl)-2-oxo-5-(phenylmethoxy)hexahydro-2H-cyclopenta[b]furan] in 85% yield.

To a solution of compound 7 (250 g, 0.64 mol) in toluene (2.5 L) at −78° C. was slowly added a solution of 1M diisobutylaluminum hydride (DIBAL-H) in dichloromethane (16 mol) over 10 minutes. The mixture was stirred for 2 hours. After completion of the reaction, methanol (300 mL) was added, followed by saturated sodium potassium tartrate solution (3 L) and the mixture was stirred for 1 hour while allowed to warm to room temperature. The organic layer was separated and the aqueous layer was extracted with ethyl acetate (3 L). The combined organic phase was washed with brine, dried over sodium sulfate and then concentrated to dryness under vacuum. The crude material was further purified by column chromatography (ethyl acetate/heptanes) to give compound 8 [(3aR,4R,5R,6aS)-4-((E)-4,4-difluoro-3-hydroxy-1-octenyl)-5-(phenylmethoxy)hexahydro-2H-cyclopenta[b]furan-2-ol in 80% yield.

To a suspension of (4-carboxybutyl)triphenyl phosphonium bromide (667 g, 1.52 mol) in anhydrous tetrahydrofuran (3 volumes) was added potassium tert-butoxide (341.3 g, 3.03 mol) at 0° C. and the mixture was stirred for 50 minutes before warming to room temperature. A solution of compound 8 (200 g, 0.506 mol) in tetrahydrofuran (700 mL) was added to the above mixture and the stirring continued for 3 hours. After the completion of the reaction, 1 N hydrochloric acid (2 L) was added. The organic layer was separated and the aqueous layer was extracted with ethyl acetate (6.50 L). The combined organic phase was washed with water and brine, dried over sodium sulfate and concentrated to dryness. Compound 9 [(Z)-7-[(1R,2R,3R,5S)-2-((E)-4,4-difluoro-3-hydroxy-1-octenyl)-3-(phenylmethoxy)-5-hydroxycyclopentyl]-5-heptenoic acid was obtained by chromatographic purification (ethyl acetate/heptanes) to in 90% yield.

To a solution of compound 9 (210 g, 0.437 mol) in dichloromethane (1.2 L) was added Dess-Martin reagent (371 g, 0.874 mol) and the mixture was stirred for 2 hours. After the completion of the reaction, a saturated sodium bicarbonate solution (1.2 L) was added and the layers were separated. The organic layer was washed with brine, dried over sodium sulfate and then concentrated to dryness under vacuum. Purified compound 10 [(Z)-7-[(1R,2R,3R)-2-((E)-4,4-difluoro-3-oxo-1-octenyl)-3-(phenylmethoxy)-5-oxocyclopentyl]-5-heptenoic acid was obtained by chromatographic purification (ethyl acetate/heptanes) to in 75% yield.

To a solution of compound 10 (150 g) in dichloromethane (15 volumes), was added 10% palladium on carbon (35% wt) and the suspension was hydrogenated at 2 PSI for 15 hours. After the completion of the reaction, the mixture was filtered through Celite®, concentrated to near dryness and purified by column chromatography (ethyl acetate in hexanes) to give crude Lubiprostone. To a solution of crude Lubiprostone in ethyl acetate (10 vol) was added tert-butylamine (1.05 eq) at room temperature. The mixture was stirred at room temperature until precipitation of the amine salt occurred. The amine salt was isolated by filtration and dried to give Lubiprostone tert-butylamine salt (20 g). The amine salt was suspended in ethyl acetate (6 volumes) and water (3 volumes). The resulting bi-phasic mixture was adjusted to about pH 5 with formic acid. The organic layer was separated and concentrated to obtain Lubiprostone as a syrup. Upon crystallization using ethyl acetate/petroleum ether (1:9 volumes), the syrup produced Lubiprostone (1, 12 g) in approximately 70% recovery. The Lubiprostone filtrate was concentrated to near-dryness. HRMS (ESI$^+$) [M+NH$_4$]$^+$ of (1): Formula: C$_{20}$H$_{36}$F$_2$NO$_5$: cal m/z: 408.25561 amu. found: 408.25626 amu.

To the concentrated Lubiprostone filtrate (10.75 g) was added ethyl acetate (2 volumes). The mixture was stirred at room temperature until dissolution was achieved. To the mixture was added hexanes (6 volumes). The mixture was stirred at room temperature for about 2 hours, stored in a freezer overnight whereupon it was stirred at −5° C. for 2 hours. The solid was isolated by filtration. The solid was purified by stirring in ethyl acetate (2 volumes) and hexanes (10 volumes) at room temperature overnight. A product was isolated by filtration, washed and dried under vacuum to give APO-II (>99.5% pure by HPLC, 6.18 g) as depicted in the PXRD diffractogram in FIG. 1, the FTIR spectrum in FIG. 2 and the DSC thermogram in FIG. 3.

Example 2

Preparation of APO-II

The procedure outlined in Example 1 to obtain the concentrated Lubiprostone filtrate was followed. To the concentrated Lubiprostone filtrate (300 mg) was added ethyl acetate (1 volume). The mixture was stirred at room temperature until dissolution was achieved. To the mixture was added petroleum ether (3 volumes). The mixture was stirred at room temperature until precipitation occurred. A product was isolated by filtration, washed and dried under vacuum to give APO-II (230 mg).

Example 3

Preparation of APO-II

To Lubiprostone (460 mg) was added ethyl acetate (1 volume) at room temperature. The mixture was stirred until dissolution was achieved. To the solution was added hexanes (3 volumes) and APO-II (2 mg, as obtained from the process described in examples 1 or 2) The mixture was stirred at room temperature for 2-4 hours until precipitation occurred. The product was isolated by filtration, washed and dried under vacuum to give APO-II (>99.5% pure by HPLC, 400 mg).

Example 4

Preparation of APO-II

To Lubiprostone (300 mg) was added ethyl acetate (1 volume) at room temperature. The mixture was stirred until dissolution was achieved. The solution was added into a mixture of hexanes (3 volumes) and APO-II (1.5 mg, as obtained from the process described in examples 1 or 2) at room temperature. The mixture was stirred for 2-4 hours until precipitation occurred. The product was isolated by filtration, washed and dried under vacuum to provide APO-II (230 mg).

Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way. Numeric ranges are inclusive of the numbers defining the range. Furthermore, numeric ranges are provided so that the range of values is recited in addition to the individual values within the recited range being specifically recited in the absence of the range. The word "comprising" is used herein as an open-ended term, substantially equivalent to the phrase "including, but not limited to", and the word "comprises" has a corresponding meaning. As used herein, the singular forms "a", "an" and "the" include plural references unless the context clearly dictates otherwise. Thus, for example, reference to "a thing" includes more than one such thing. Citation of references herein is not an admission that such references are prior art to the present invention. Furthermore, material appearing in the background section of the specification is not an admission that such material is prior art to the invention. Any priority document(s) are incorporated herein by reference as if each individual priority document were specifically and individually indicated to be incorporated by reference herein and as though fully set forth herein. The invention includes all embodiments and variations substantially as hereinbefore described and with reference to the examples and drawings.

What is claimed is:

1. A crystalline form of Lubiprostone having an X-ray powder diffraction pattern acquired using CuKα radiation comprising peaks, in terms of 2-theta, at approximately 8.98, 13.53, 18.06 and 22.74.

2. The crystalline form of Lubiprostone of claim 1 wherein the X-ray powder diffraction pattern further comprises a peak, in terms of 2-theta, at approximately 20.80.

3. The crystalline form of Lubiprostone of claim 2 having a 1% KBr FTIR spectrum comprising peaks, in terms of $cm_{-1}$, at approximately 3470, 2938, 1738, 1710, 1473, 1383, 1313, 1210, 1159, 979, 891, 793, 726 and 580.

Figure 2:
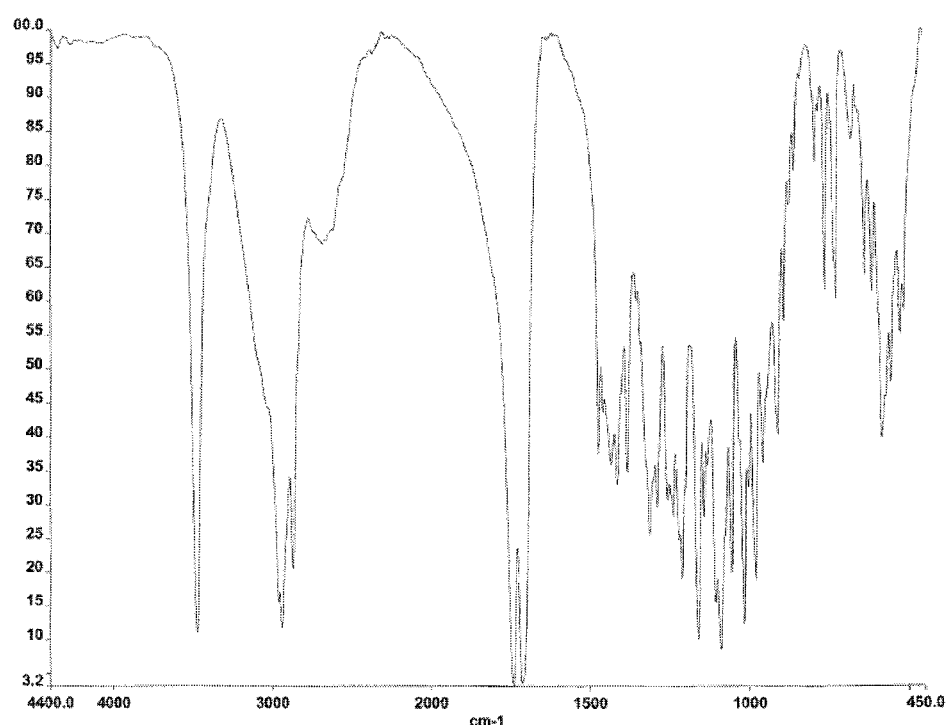
FIG. 2: is a Fourier transform infrared (FTIR) spectrum of APO-II.

4. The crystalline form of Lubiprostone of claim 2 having a FTIR spectrum substantially as shown in FIG. 2.

5. The crystalline form of Lubiprostone of claim 2 having a DSC thermogram comprising an endothermic peak with a peak onset temperature of approximately 76° C. and a peak maximum of approximately 77° C.

Figure 3:
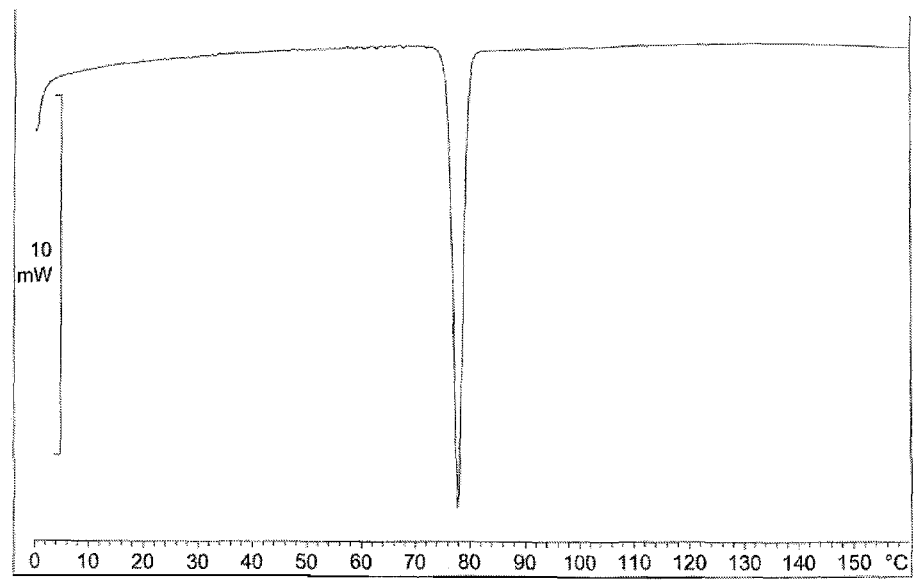
FIG. 3: is a differential scanning calorimetry (DSC) thermogram of APO-II.

6. The crystalline form of Lubiprostone of claim 2 having a DSC thermogram substantially as shown in FIG. 3.

7. The crystalline form of Lubiprostone of claim 1 wherein the X-ray powder diffraction pattern further comprises a peak, in terms of 2-theta, at approximately 20.57.

8. The crystalline form of Lubiprostone of claim 7 having a 1% KBr FTIR spectrum comprising peaks, in terms of $cm_{-1}$, at approximately 3470, 2938, 1738, 1710, 1473, 1383, 1313, 1210, 1159, 979, 891, 793, 726 and 580.

9. The crystalline form of Lubiprostone of claim 7 having a FTIR spectrum substantially as shown in FIG. 2.

10. The crystalline form of Lubiprostone of claim 7 having a DSC thermogram comprising an endothermic peak with a peak onset temperature of approximately 76° C. and a peak maximum of approximately 77° C.

11. The crystalline form of Lubiprostone of claim 7 having a DSC thermogram substantially as shown in FIG. 3.

12. The crystalline form of Lubiprostone of claim 1 having a 1% KBr FTIR spectrum comprising peaks, in terms of $cm_{-1}$, at approximately 3470, 2938, 1738, 1710, 1473, 1383, 1313, 1210, 1159, 979, 891, 793, 726 and 580.

13. The crystalline form of Lubiprostone of claim 1 having a FTIR spectrum substantially as shown in FIG. 2.

14. The crystalline form of Lubiprostone of claim 1 having a DSC thermogram comprising an endothermic peak with a peak onset temperature of approximately 76° C. and a peak maximum of approximately 77° C.

15. The crystalline form of Lubiprostone of claim 1 having a DSC thermogram substantially as shown in FIG. 3.

16. A crystalline form of Lubiprostone having an X-ray powder diffraction pattern acquired using CuKα radiation substantially as shown in FIG. 1.

17. The crystalline form of Lubiprostone of claim 16 having a 1% KBr FTIR spectrum comprising peaks, in terms of $cm_{-1}$, at approximately 3470, 2938, 1738, 1710, 1473, 1383, 1313, 1210, 1159, 979, 891, 793, 726 and 580.

18. The crystalline form of Lubiprostone of claim 16 having a FTIR spectrum substantially as shown in FIG. 2.

19. The crystalline form of Lubiprostone of claim 16 having a DSC thermogram comprising an endothermic peak with a peak onset temperature of approximately 76° C. and a peak maximum of approximately 77° C.

20. The crystalline form of Lubiprostone of claim 16 having a DSC thermogram substantially as shown in FIG. 3.

* * * * *